US006984221B1

(12) United States Patent
Scheye

(10) Patent No.: US 6,984,221 B1
(45) Date of Patent: Jan. 10, 2006

(54) DEVICE FOR PROVIDING FLUID COMMUNICATION WITH A HOLLOW VISCUS AT THE SKIN SURFACE

(76) Inventor: Thierry Scheye, 12, rue Volney, 63000 Clermont-Ferrand (FR)

(*) Notice: Subject to any disclaimer, the term of this patent is extended or adjusted under 35 U.S.C. 154(b) by 0 days.

(21) Appl. No.: 09/936,582

(22) PCT Filed: Mar. 15, 2000

(86) PCT No.: PCT/FR00/00618

§ 371 (c)(1),
(2), (4) Date: Sep. 20, 2001

(87) PCT Pub. No.: WO00/54727

PCT Pub. Date: Sep. 21, 2000

(30) Foreign Application Priority Data

Mar. 15, 1999 (FR) .................................. 99 03897

(51) Int. Cl.
*A61M 5/32* (2006.01)

(52) U.S. Cl. ...................................................... 604/178

(58) Field of Classification Search .................. 604/48, 604/93.01, 104, 105, 106, 107, 108, 109, 604/158, 164.01, 174, 175, 178, 264, 274, 604/278, 523, 533, 534, 535, 536, 539, 910
See application file for complete search history.

(56) References Cited

U.S. PATENT DOCUMENTS

| | | | | |
|---|---|---|---|---|
| 4,315,513 | A | 2/1982 | Nawash et al. | |
| 4,344,435 | A | 8/1982 | Aubin | |
| 5,374,254 | A | 12/1994 | Buma | |
| 5,391,156 | A * | 2/1995 | Hildwein et al. | 604/174 |
| 5,411,491 | A | 5/1995 | Goldhardt et al. | |
| 5,484,420 | A | 1/1996 | Russo | |

FOREIGN PATENT DOCUMENTS

| | | |
|---|---|---|
| GB | 2169808 | 7/1986 |

* cited by examiner

*Primary Examiner*—Nicholas D. Lucchesi
*Assistant Examiner*—Mark K. Han
(74) *Attorney, Agent, or Firm*—Horst M. Kasper

(57) ABSTRACT

The invention concerns a device for providing fluid communication with a hollow viscus at the skin surface. Said device, which comprises a tube integral at its ends with intravisceral (8) and cutaneous (6) support flanges, is characterized in that the tube consists of two parts (2,4) integral with a respective flange (6, 8), mounted axialy mobile for their relative but not spontaneously reversible displacement, the tube part (4) integral with the intravisceral flange (8), comprising external locking means (10, 12, 26) enabling the practitioner to perform said length on the basis of the cumulated thickness of the patient's walls through which it passes.

26 Claims, 1 Drawing Sheet

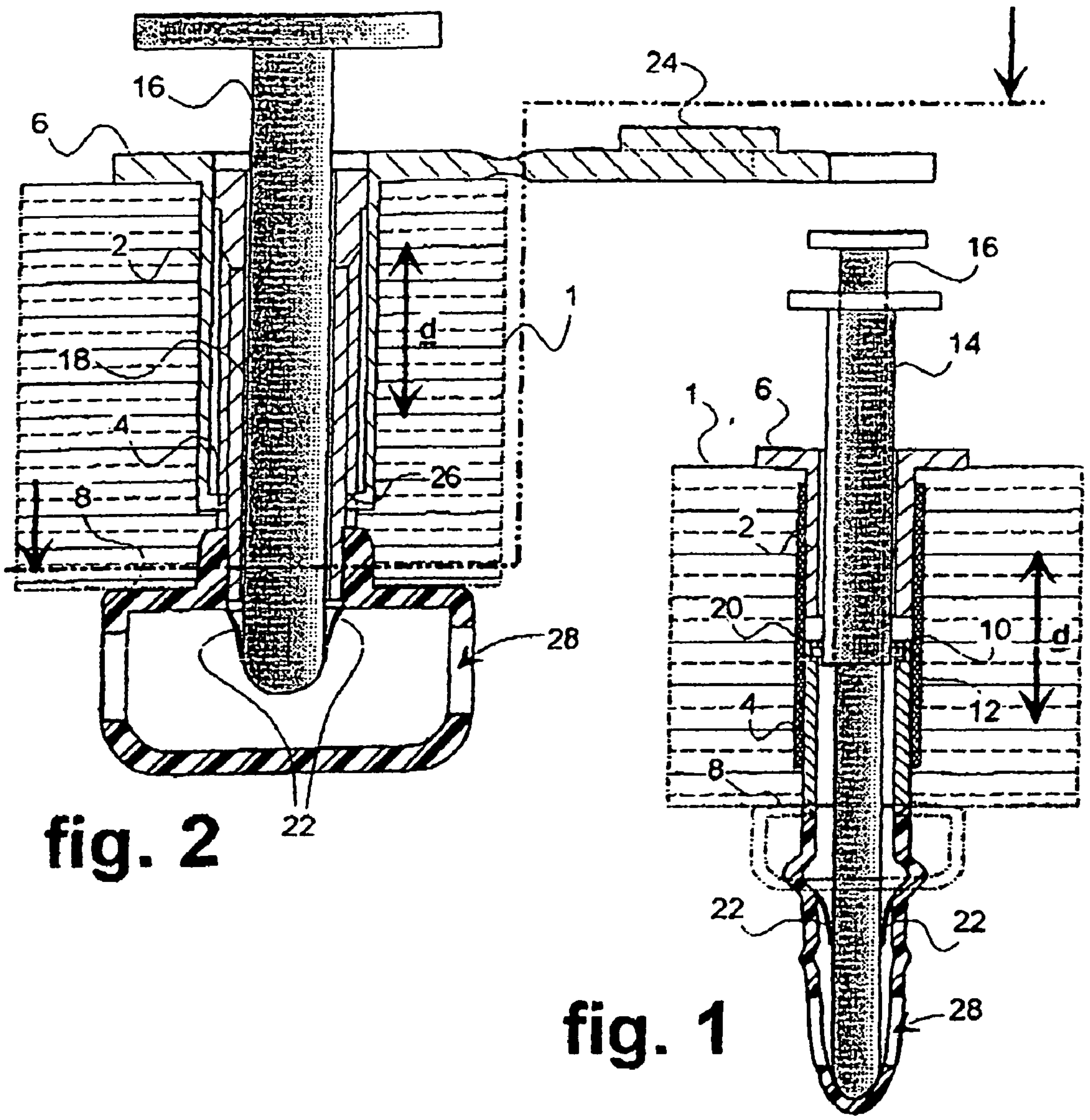
fig. 2
fig. 1
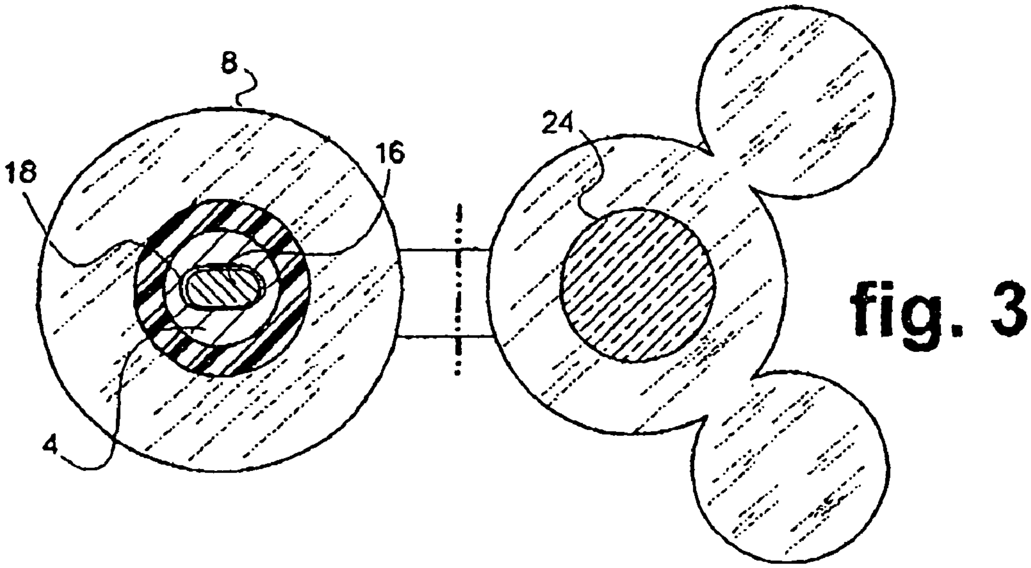
fig. 3

DEVICE FOR PROVIDING FLUID COMMUNICATION WITH A HOLLOW VISCUS AT THE SKIN SURFACE

The invention comes under the field of medical instrumentation and concerns a device for inosculation of a hollow organ to the skin.

There is a known medical technique for inosculation of a hollow organ to the skin. This technique can be used for various organs such as the stomach, colon, small intestine or the bladder and uses a device designed to provide communication between the outside of the body and the inside of the organ. Generally speaking this kind of device comprises principally a transparietal tube with elements at each end, such as or similar to collars, that press respectively against the inside wall of the organ and the outer surface of the skin: these collars are termed respectively intravisceral and skin collars.

These devices can be divided into two types, the first being described, for example, by U.S. Pat. No. 4,344,435 (AUBIN), U.S. Pat. No. 5,374,254 (BUMA) and U.S. Pat. No. 5,484,420 (RUSSO), for which the distal end of the transparietal tube possesses a shoulder forming the intravisceral collar, with the other end of the tube designed to protrude from the patient's body and shaped to take the skin collar on the outside, whether this is screwed on (U.S. Pat. No. 4,344,435), clipped on (U.S. Pat. No. 5,374,254) or hard push fitted (U.S. Pat. No. 5,484,420), for example. These devices are fitted on the patient either by introducing the tube via the oesophagus until the proximal end of the tube emerges from an incision in the patient's skin (U.S. Pat. No. 5,374,254) and (U.S. Pat. No. 5,484,420), or by making an incision in the patient's body large enough to allow the intravisceral collar to be introduced (U.S. Pat. No. 4,344, 435).

The disadvantage with this first type of device is that surgery and anaesthesia are necessary for them to be installed. In addition they are more particularly designed to work with a specific fitting installed permanently for the whole period of treatment, and are uncomfortable for the patient notably because they protrude from the body at all times.

This is the reason why a second type of device was developed, the so-called "button", where almost the whole length of the tube lies within the wall of the body to avoid the discomfort of any protrusion. With most of these devices an opening is first made in the patient's body and allowed to heal, after which the intravisceral collar, the shape of which can be altered sufficiently to pass through the opening easily, can be introduced directly from the outside. The practitioner alters the shape of the intravisceral collar when installing the button, notably using a pusher that can be inserted inside the tube. Finally a shutter is often provided to close the transparietal tube when not in use. This type of device is described notably in patents GB2169808 (HABERMAN) and U.S. Pat. No. 4,325,513 (NAWASH) and also in patent U.S. Pat. No. 5,374,254 referred to above, that has an arrangement to transform the first type of device into the second type, by cutting the tube after installation and closing it with a shutter.

A more general problem posed by the above-mentioned inosculation devices lies in the fact that the cumulated thickness of fascia crossed varies from one patient to another, and also according to where the device is installed on the patient, and even for the same place and same patient from one point in time to another; for example, in the case of gastrostomy when the patient gains weight during treatment this results in the abdominal wall growing thicker thus rendering inadequate the button installed at the outset.

Note that this problem is solved when devices of the first type are installed on the patient, thanks to the fact that the tube on which the skin collar is installed protrudes from the skin so that the collar can be adjusted as required on the patient, and even for devices U.S. Pat. No. 4,344,435 and U.S. Pat. No. 5,484,420, for which during treatment the screwed or sliding connection of the collar on the tube can be adjusted and thus allow changes in the distance separating the two collars one from the other as required.

In order to overcome this problem for devices of the second type, sets of buttons have been proposed where the respective length of the tube varies, so that the practitioner chooses the one most suited to the case in hand. However this answer is not totally satisfactory because it may happen that none of the buttons available in the set has a tube length corresponding exactly to what is needed.

Buttons have also been proposed in which the collar that holds the tube against the inside wall of the organ and the shape of which can be modified, is balloon shaped to allow for a relative change in the distance separating the two collars one from the other. However in practice it has been found that the balloon, that is inflated with normal saline, tends to rupture especially if the patient moves abruptly, such as for example when coughing or when straining with the abdominal muscles due to constipation.

Finally there was another proposal, notably with patent GB2169808 (HABERMAN), to have a sliding fit for the intravisceral collar on the transparietal tube, so that when the button is installed the intravisceral collar can be brought more or less close to the skin collar according to the patient in question, by means of traction on the intravisceral collar using pull threads. However, although this answer avoids the need of having to place a large number of collars in a set at the practitioners disposal, it does not allow the distance between the collars to be adjusted during treatment, notably to allow for the patient's weight gain. This function that is adjustable only when the device is installed on the patient is highlighted by the fact that the threads that are used to hold the intravisceral collar are designed to be either broken down by the gastric juices or to be resorbable. Finally it should be noted that contradictory functions are required of the means of connection between the intravisceral collar and the tube, because this connection has to be both rigid enough for satisfactory stability of the device on the patient and yet allow for slippage when the position of the intravisceral collar needs to be adjusted.

Generally speaking it can be seen that none of the devices of the first nor of the second type of device described above has any means of adjusting the distance separating the intravisceral and skin collars during treatment, except for the configuration in which the transparietal tube protrudes from the patient's body to receive the skin collar and which is not comfortable for the patient. In other words, the second type of device, the so-called buttons, do not possess the said means of adjustment except for by using the same method as the first type of device, i.e. making the tube protrude from the patient's body, in which case this second type no longer complies with the criteria of comfort that prompted their design.

The device presented with this invention is a device for inosculation of a hollow organ to the skin, along the same lines as the second type of device described above, i.e. the so-called button, comprising a transparietal tube the ends of which are attached to collars that hold the tube respectively against the internal wall of the organ (intravisceral collar)

and against the outside surface of the skin (skin collar), with the intravisceral collar designed so that its shape can be changed by the practitioner using notably a pusher, to allow it to pass inside the organ directly from outside the patient's body. Note that with these button type devices the axial dimension lies within that of the two intravisceral and skin collars in order to be comfortable for the patient. For example the intravisceral collar forms the base of a hollow body, the shape of which is changed by the practitioner using a pusher that is introduced inside the tube, with the said hollow body comprising lateral openings so that liquids can pass through the liquids tube between the organ and the outside.

The purpose of the present invention is to offer a device of the type described above that can be installed and adapted for a given patient, according to the thickness of the walls involved, whilst ensuring that the patient's comfort is not affected by an awkward protrusion of the tube outside his body.

With the present invention, and based on the analysis above that contributes to the inventive approach to this invention, a device of the type described above comprises a transparietal tube made up of at least two parts, each attached respectively to the intravisceral and to the skin collar. These parts of the transparietal tube are fitted so as to be mobile for the relative change in axial position in a fashion that is not spontaneously reversible. The so-called distal part of the tube that is attached to the intravisceral collar has means of rendering it immobile working from the outside to the inside of the tube, so that the practitioner can make the said change in position. These arrangements are such that the practitioner can adapt the length of the tube in both directions, according to the cumulated thickness of the fascia crossed in the patient, both at the time and after installation of the tube on the patient, and such that the variation in length of the tube is taken up in the thickness of the patient's fascia that it crosses, that is to say in other terms that the variation in the length of tube, notably with respect to lengthening, does not change the initial distance it protruded from the patient's body.

The result of these arrangements is that a variation in the distance between the intravisceral and skin retention collars is now possible, including after installation of the device on the patient, with the said variation being obtained by a deliberate procedure carried out by the practitioner and having no adverse effect, neither on the reliability of the device in place, nor on how comfortable it is for the patient.

It should be understood that according to various variations similar at this general stage of the invention, the said two proximal and distal parts of the transparietal tube are fitted so as to be mobile in coaxial fashion, either one upon the other or again each relative to an intermediary body.

In the case that the intravisceral collar is designed to have its shape changed by the practitioner using a pusher that is introduced inside the tube, the distal part of the tube is best designed in order to enable it to be gripped by the pusher to render it immobile, with this aspect of the design being for example of the bayonet type in the event that mobility of the parts of the tube relies upon sliding, or again by a non circular type of nesting fit for the pusher via the axial opening of the distal part of the tube, in the event that the mobility of the parts of the tube relies upon a screw action. These arrangements enable the practitioner to adapt the length of transparietal tube using the pusher, at least the initially when the tube is installed on the patient.

It should be understood that a pusher comprising arrangements that are complementary to those of the distal part of the tube for the said immobilisation of the latter, are part of the device covered by the invention.

The relative mobility between the two parts of the transparietal tube is preferably obtained by a screwing movement. The distal part of the tube is for example designed with a non circular axial opening that forms the said nesting organ, so that it can be immobilised in the rotational direction by the practitioner using a specific tool. This tool can be introduced into the said axial opening of the distal part of the tube, and comprises at least one area of complementary cross-section.

In the preferred form for constructing the invention, the distal and proximal parts of the transparietal tube are connected one to the other by screwing, and advantage is taken of the pusher used to change the shape of the intravisceral collar to immobilise the distal part of the tube in the rotational direction. To this end the pusher, or a specific tool of the type described above, comprises for example a non circular section between its two ends designed to traverse the axial opening of complementary shape in the distal part of the tube.

With another approach to the invention, the transparietal tube is "telescopic". By "telescopic" should be understood in general the capacity conferred upon the transparietal tube to change its axial dimension. The tube comprises at least two end parts, each respectively attached to the intravisceral and skin collars, that are mobile in an axial direction one relative to the other in order to enable the length of the tube to be varied. The distal part at least, if not both parts of the tube, can be rendered immobile from the outside, notably using a tool designed to grip the distal part of the tube to enable the practitioner to change the length of the tube, in both directions, after installing the device on the patient.

It will be more easy to understand the invention and the details concerning it in the description that is going to be made of a preferred form of construction, by referring to the drawings on the appended sheet, in which:

FIG. 1 is a diagrammatic view along the axis, of a device using a first form of construction for the invention, where the shape of the intravisceral collar is being changed by a pusher, FIG. 2 is an axial view of a device according to a second type of construction for the invention, and is the preferred type, FIG. 3 is a partial transverse section view of the device illustrated in the previous figure.

On these drawings, a device for inosculation of a hollow organ to the skin comprises principally a tube in two parts 2 and 4, each of these parts 2 and 4 being attached to a retention collar, 6 and 8, respectively against the internal wall of the organ for the distal part 4 of the tube, and against the external surface of the skin for the proximal part 2 of the tube. The two parts 2 and 4 or the tube are mobile in an axial direction one relative to the other, with the possibility of rendering the distal part 4 of the tube immobile from the outside in order to enable the practitioner to vary the length of tube 2, 4, including when the device has been installed on the patient.

Note that a variation in the distance d separating the collars 6 and 8 one from the other is absorbed by a corresponding variation in the cumulated thickness of the fascia 1 of the patient crossed by tube 2, 4, with any variation in the said distance d inducing consequently a simultaneous variation of the length of the tube 2, 4 lying between the two collars 6 and 8.

On the variation illustrated in FIG. 1, the relative mobility between parts 2 and 4 of the tube is obtained by parts 2 and 4 sliding axially one relative to the other. Immobilisation of the distal part 4 of the tube is obtained by means of a "bayonet" device 10, 12, with slots 10 being provided on the distal part 4 of the tube to allow the latter to be held by a specific tool 14 provided with lugs 12.

On the variation illustrated in FIG. 2 the said relative mobility between parts 2 and 4 of the tube is obtained by screwing, by means of the tapping 26, with parts 2 and 4 composing the transparietal tube being preferably two in number and being screwed one into the other.

Immobilisation of the distal part 4 of the tube is obtained by means of pusher 16 generally used by the practitioner to push the intravisceral collar 8 out of shape when installing the device on a patient.

By referring to FIG. 3, it will be noted that immobilisation in the rotational direction of the distal part 4 of the tube is obtained thanks to the non circular shape of the axial opening 18 of the distal part 4 of, the latter being traversed by an area of the pusher 18 having a cross-section of complementary shape.

It will be understood that having the transparietal tube in two parts 2 and 4 as illustrated in FIG. 2 is a preference only, and that in equivalent manner the transparietal tube could include an intermediate part in addition, such as 20 on the example illustrated in FIG. 1, without escaping the general rule of the invention described.

The device covered by the invention is preferably provided, in similar fashion to previous devices for this purpose, with a spontaneously closing valve 22 on the distal end of the tube, and a movable shutter 24 on the proximal end of the tube. Note also the presence as usual in this context, of lateral openings 28 made in the hollow body forming intravisceral collar 8.

Note also that immobilisation of the proximal part 2 of the tube can be obtained using the skin collar 6, that can be easily gripped from outside.

In addition, the distal part 4 of the tube can be held to advantage from the inside of the transparietal tube using a removable instrument, such as 14 or 16 in the manner illustrated, to enable the distal part 4 of the tube to be held immobile by the practitioner without the said tool 14 or 16 protruding unpleasantly from the patient's body on a permanent basis.

As an indication, the proportional variation in the distance separating the two collars one from the other is of the order of 0.5 to 1 times the minimal length of the tube, depending on the size of the latter. For example, for a tube with minimum length 1 cm, the maximum length of the tube will be about 1.5 cm; for a tube measuring a minimum length of 3 cm, the maximum length of the tube will be about 6 cm.

Note finally that the applications for the device covered by the invention are not limited to human surgery, but can be used also for veterinary surgery.

What is claimed is:

1. Device for inosculation of a hollow organ to the skin, of the type of device comprising a transparietal tube, ends of which are attached to collars (6, 8) holding the tube, respectively, against the internal wall of the organ (intravisceral collar 8) and against the outside surface of the skin (skin collar 6), with the intravisceral collar (8) being constructed so that its shape can be changed by the practitioner to allow the intravisceral collar (8) to pass inside the organ directly from the outside of the patient's body, with the following characteristics:

The transparietal tube comprises at least two parts (2, 4), each attached to a collar respectively intravisceral (8) and skin (6), the said parts (2, 4) of the tube being fitted so that they are mobile for relative changes axial in position that are not spontaneously reversible, the said distal part (4) of the tube, attached to the intravisceral coller (8), comprising means of immobilisation (10, 12, 26) that can be used from the outside towards the inside of the tube to enable the practitioner to make the said changes in position; Such that the practitioner can adapt the length of the tube (2, 4), in both directions, according to the cumulated thickness of the fascia (1) of the patient crossed, both at the time and after the tube (2, 4) is installed on the patient, and such that the variation in the length of the tube is taken up inside the thickness of the fascia (1) of the patient that it crosses;

The relative mobility between the two parts (2, 4) of the transparietal tube is obtained by screwing (26), with the distal part (4) of the tube being provided with a non circular axial opening (18) that constitutes a nesting organ, in order for it to be rendered immobile in the rotational direction by the practitioner using a specific tool (16), that can be introduced inside the said axial opening (18) and that comprises at least one area of complementary cross-section.

2. Device according to claim 1, with the following characteristics:

the transpariental tube (2, 4) is "telescopic" and comprises at least two end parts (2, 4) making up the said distal (4) and proximal (2) parts of the tube.

3. Device according to claim 2, with the following characteristics:

the distal (4) and proximal (2) parts of the tube are connected one to the other by screwing (26).

4. Device according to claim 1, with the following characteristics:

the relative mobility between the parts (2, 4) of the tube is obtained by the parts (2, 4) sliding axially one relative to the other, with the distal part (4) of the tube being rendered immobile by means of a "bayonet" device (10, 12), with slots (10) being provided in the distal part (4) of the tube in order to allow the latter to be gripped by a specific tool (14) provided with lugs (12).

5. Device for inosculation of a hollow organ to the skin, of the type of device comprising a transparietal tube, ends of which are attached to collars (6, 8) holding the tube, respectively, against the internal wall of the organ (intravisceral collar 8) and against the outside surface of the skin (skin collar 6), with the intravisceral collar (8) being constructed so that its shape can be changed by the practitioner to allow the intravisceral collar (8) to pass inside the organ directly from the outside of the patient's body, with the following characteristics:

The transparietal tube comprises at least two parts (2, 4), each attached to a collar respectively intravisceral (8) and skin (6), the said parts (2, 4) of the tube being fitted so that they are mobile for relative changes axial in position that are not spontaneously reversible, the said distal part (4) of the tube, attached to the intravisceral coller (8), comprising means of immobilisation (10, 12, 26) that can be used from the outside towards the inside of the tube to enable the practitioner to make the said changes in position; Such that the practitioner can adapt the length of the tube (2, 4), in both directions, according to the cumulated thickness of the fascia (1) of the patient crossed, both at the time and after the tube (2, 4) is installed on the patient, and such that the variation in the length of the tube is taken up inside the thickness of the fascia (1) of the patient that it crosses, where a shape of the intravisceral collar (8) can be changed by the practitioner by means of a pusher (16) that can be introduced inside the tube (2, 4), with the following characteristics:

The distal part (4) of the tube is specially designed to enable it to be gripped by the pusher (16) in order to render it immobile, Such that the practitioner can adapt the length of transparietal tube (2, 4) using the pusher (16) at least initially when the tube (2, 4) is installed on the patient.

6. Device according to claim 5, with the following characteristics:

The pusher (16) comprises between its two ends a non circular section designed to traverse the axial opening (18) of complementary shape in the distal part (4), in order to render the distal part (4) immobile in the rotational direction.

7. A device for inosculation of a hollow organ to the skin, comprising a first part (2) of a transparietal tube having a first end and a second end;

a second part (4) of the transparietal tube having a first end and a second end;

a skin collar (6) attached to and holding the first end of the first part (2) of the transparietal tube against an outside surface of a skin;

an intravisceral collar (8) attached to and holding the first end of the second part (4) of the transparietal tube against an internal wall of the hollow organ, wherein the intravisceral collar (8) is constructed such that a shape of the intravisceral collar (8) is changeable by the practitioner to allow the intravisceral collar (8) to pass inside the organ directly from the outside of the patient's body;

wherein the first part (2) of the transparietal tube and the second part (4) of the transparietal tube are fitted so that they are mobile axial for relative changes in position that are not spontaneously reversible, wherein the second part (4) of the tube is attached to the intravisceral collar (8);

an adjustment arrangement (10, 12, 26) that engageable from the outside towards the inside of the transparietal tube to enable a practitioner to make changes of a relative position of the first part (2) of the transparietal tube relative to the second part (4) of the transparietal tube such as to enable the practitioner to increase or to decrease a length of the transparietal tube according to a cumulated thickness of a fascia (1) of a patient crossed, both at a time of installation of the transparietal tube and after the transparietal tube has been installed on the patient, and wherein a change in the length of the transparietal tube is taken up inside the thickness of the fascia (1) of the patient crossed by the transparietal tube, wherein a relative mobility between the first part (2) of the transparietal tube and the second part (4) of the transparietal tube is obtained by the first part (2) of the transparietal tube and the second part (4) of the transparietal tube (4) sliding axially one relative to the other, wherein the second part (4) of the transparietal tube is rendered immobile by means of a "bayonet" device (10, 12), and wherein slots (10) are furnished in the second part (4) of the transparietal tube in order to allow the transparietal tube to be gripped by a specific tool (14) provided with lugs (12).

8. The device according to claim 7, wherein the transparietal tube is "telescopic" and comprises the first part (2) and the second part (4) making up a proximal part (2) and a distal part (4) of the transparietal tube.

9. The device according to claim 8, wherein the distal part (4) and the proximal part (2) of the transparietal tube are connected one to the other by screwing (26).

10. A device for inosculation of a hollow organ to the skin, comprising a first part (2) of a transparietal tube having a first end and a second end;

a second part (4) of the transparietal tube having a first end and a second end;

a skin collar (6) attached to and holding the first end of the first part (2) of the transparietal tube against an outside surface of a skin;

an intravisceral collar (8) attached to and holding the first end of the second part (4) of the transparietal tube against an internal wall of the hollow organ, wherein the intravisceral collar (8) is constructed such that a shape of the intravisceral collar (8) is changeable by the practitioner to allow the intravisceral collar (8) to pass inside the organ directly from the outside of the patient's body;

wherein the first part (2) of the transparietal tube and the second part (4) of the transparietal tube are fitted so that they are mobile axial for relative changes in position that are not spontaneously reversible, wherein the second part (4) of the tube is attached to the intravisceral collar (8);

an adjustment arrangement (10, 12, 26) that engageable from the outside towards the inside of the transparietal tube to enable a practitioner to make changes of a relative position of the first part (2) of the transparietal tube relative to the second part (4) of the transparietal tube such as to enable the practitioner to increase or to decrease a length of the transparietal tube according to a cumulated thickness of a fascia (1) of a patient crossed, both at a time of installation of the transparietal tube and after the transparietal tube has been installed on the patient, and wherein a change in the length of the transparietal tube is taken up inside the thickness of the fascia (1) of the patient crossed by the transparietal tube, wherein a shape of the intravisceral collar (8) is changeable by the practitioner by means of a pusher (16), wherein the pusher is introduceable inside the transparietal tube, wherein the second part (4) of the transparietal tube is constructed to enable the transparietal tube to be gripped by the pusher (16) in order to render the transparietal tube immobile for allowing the practitioner to adapt the length of the transparietal tube using the pusher (16) at least initially when the transparietal tube is installed on the patient.

11. The device according to claim 10, wherein the pusher (16) comprises a non circular section between two ends of the pusher (16), wherein the non-circular section is constructed to traverse an axial opening (18) of complementary shape in the second part (4) of the transparietal tube, in order to render the second part (4) of the transparietal tube immobile in a rotational direction.

12. The device according to claim 10, wherein a relative mobility between the first part (2) of the transparietal tube and the second part (4) of the transparietal tube is obtained by the first part (2) of the transparietal tube and the second part (4) of the transparietal tube (4) sliding axially one relative to the other, wherein the second part (4) of the transparietal tube is rendered immobile by means of a "bayonet" device (10, 12), and wherein slots (10) are furnished in the second part (4) of the transparietal tube in order to allow the transparietal tube to be gripped by a specific tool (14) provided with lugs (12).

13. A device for inosculation of a hollow organ to the skin, comprising a first part (2) of a transparietal tube having a first end and a second end;

a second part (4) of the transparietal tube having a first end and a second end;

a skin collar (6) attached to and holding the first end of the first part (2) of the transparietal tube against an outside surface of a skin;

an intravisceral collar (8) attached to and holding the first end of the second part (4) of the transparietal tube against an internal wall of the hollow organ, wherein the intravisceral collar (8) is constructed such that a shape of the intravisceral collar (8) is changeable by the practitioner to allow the intravisceral collar (8) to pass inside the organ directly from the outside of the patient's body;

wherein the first part (2) of the transparietal tube and the second part (4) of the transparietal tube are fitted so that they are mobile axial for relative changes in position that are not spontaneously reversible, wherein the second part (4) of the tube is attached to the intravisceral collar (8);

an adjustment arrangement (10, 12, 26) that engageable from the outside towards the inside of the transparietal tube to enable a practitioner to make changes of a relative position of the first part (2) of the transparietal tube relative to the second part (4) of the transparietal tube such as to enable the practitioner to increase or to decrease a length of the transparietal tube according to a cumulated thickness of a fascia (1) of a patient crossed, both at a time of installation of the transparietal tube and after the transparietal tube has been installed on the patient, and wherein a change in the length of the transparietal tube is taken up inside the thickness of the fascia (1) of the patient crossed by the transparietal tube, wherein a relative mobility between the first part (2) of the transparietal tube and the second part (4) of the transparietal tube is obtained by screwing (26), wherein the second part (4) of the transparietal tube is furnished with a non circular axial opening (18) that constitutes a nesting organ, in order for the transparietal tube to be rendered immobile in a rotational direction by the practitioner using a pusher (16), which pusher (16) can be introduced inside the said axial opening (18) and which pusher comprises at least one area of complementary cross-section.

14. The device according to claim 13, wherein a relative mobility between the first part (2) of the transparietal tube and the second part (4) of the transparietal tube is obtained by the first part (2) of the transparietal tube and the second part (4) of the transparietal tube (4) sliding axially one relative to the other, wherein the second part (4) of the transparietal tube is rendered immobile by means of a "bayonet" device (10, 12), and wherein slots (10) are furnished in the second part (4) of the transparietal tube in order to allow the transparietal tube to be gripped by a specific tool (14) provided with lugs (12).

15. A device for inosculation of a hollow organ to the skin, comprising a first part (2) of a transparietal tube having a first end and a second end;

a second part (4) of the transparietal tube having a first end and a second end, wherein the first part (2) of the transparietal tube and the second part (4) of the transparietal tube are fitted to each other for allowing to induce a relative shifting in an axial direction of the first part (2) of the transparietal tube relative to the second part (4) of the transparietal tube such that the shifting is not spontaneously reversible;

a skin collar (6) attached to and holding the first end of the first part (2) of the transparietal tube against an outside surface of a skin;

an intravisceral collar (8) attached to and holding the first end of the second part (4) of the transparietal tube against the internal wall of a hollow organ, wherein the intravisceral collar (8) is constructed such that a shape of the intravisceral collar (8) is elastically deformable to allow the intravisceral collar (8) to pass inside the hollow organ directly from an outside of a patient's body;

a bayonet device (10, 12) having slots (10) furnished on the second part (4) of the transparietal tube, wherein the bayonet device (10, 12) is engageable from the outside towards the inside of the transparietal tube to enable a making of changes of a relative position of the first part (2) of the transparietal tube relative to the second part (4) of the transparietal tube such as to enable an increase or a decrease a length of the transparietal tube according to a cumulated thickness of a fascia (1) of a patient crossed, both at a time of installation of the transparietal tube and after the transparietal tube has been installed on the patient, and wherein a change in the length of the transparietal tube is taken up inside the thickness of the fascia (1) of the patient crossed by the transparietal tube;

slots (10) furnished in the second part (4) of the transparietal tube in order to allow the transparietal tube to be gripped by a specific tool (14) provided with lugs (12), wherein a relative mobility between the first part (2) of the transparietal tube and the second part (4) of the transparietal tube is obtained by the first part (2) of the transparietal tube and the second part (4) of the transparietal tube (4) sliding axially one relative to the other, wherein the second part (4) of the transparietal tube is rendered immobile by means of the "bayonet" device (10, 12).

16. The device according to claim 15, further comprising an intermediate part (20) of the transparietal tube disposed between the first part of the transparietal tube and the second part (4) of the transparietal tube.

17. A device for inosculation of a hollow organ to the skin, comprising a first part (2) of a transparietal tube having a first end and a second end;

a second part (4) of the transparietal tube having a first end and a second end, wherein the first part (2) of the transparietal tube and the second part (4) of the transparietal tube are fitted to each other for allowing to induce a relative shifting in an axial direction of the first part (2) of the transparietal tube relative to the second part (4) of the transparietal tube such that the shifting is not spontaneously reversible;

a skin collar (6) attached to and holding the first end of the first part (2) of the transparietal tube against an outside surface of a skin;

an intravisceral collar (8) attached to and holding the first end of the second part (4) of the transparietal tube against the internal wall of a hollow organ, wherein the intravisceral collar (8) is constructed such that a shape of the intravisceral collar (8) is elastically deformable to allow the intravisceral collar (8) to pass inside the hollow organ directly from an outside of a patient's body;

a bayonet device (10, 12) having slots (10) furnished on the second part (4) of the transparietal tube, wherein the bayonet device (10, 12) is engageable from the outside towards the inside of the transparietal tube to enable a making of changes of a relative position of the first part (2) of the transparietal tube relative to the second part (4) of the transparietal tube such as to enable an increase or a decrease a length of the transparietal tube according to a cumulated thickness of a fascia (1) of a patient crossed, both at a time of installation of the transparietal tube and after the transparietal tube has been installed on the patient, and wherein a change in the length of the transparietal tube is taken up inside the thickness of the fascia (1) of the patient crossed by the transparietal tube, wherein the intravisceral collar (8) is shaped like an elastic bottle, wherein the shape of the elastic bottle is changeable by means of a pusher (16), wherein the pusher is introduceable inside the transparietal tube, wherein the second part (4) of the transparietal tube is constructed to enable the transparietal tube to be gripped by the pusher (16) in order to render the transparietal tube immobile for allowing the practitioner to adapt the length of transparietal tube using the pusher (16) at least initially when the transparietal tube is installed on the patient.

18. The device according to claim 17 further comprising a noncircular axial opening (18) disposed in the second part (4) of the transparietal tube, wherein the pusher (16) comprises a non circular section between two ends of the pusher (16), wherein the non-circular section is constructed to traverse the axial opening (18) of complementary shape in the second part (4) of the transparietal tube, in order to render the second part (4) of the transparietal tube immobile in a rotational direction.

19. The device according to claim 17, further comprising slots (10) furnished in the second part (4) of the transparietal tube in order to allow the transparietal tube to be gripped by a specific tool (14) provided with lugs (12), wherein a relative mobility between the first part (2) of the transparietal tube and the second part (4) of the transparietal tube is obtained by the first part (2) of the transparietal tube and the second part (4) of the transparietal tube (4) sliding axially one relative to the other, wherein the second part (4) of the transparietal tube is rendered immobile by means of the "bayonet" device (10, 12).

20. The device according to claim 17, further comprising an intermediate part (20) of the transparietal tube disposed between the first part of the transparietal tube and the second part (4) of the transparietal tube.

21. A device for inosculation of a hollow organ to the skin, comprising a first part (2) of a transparietal tube having a first end and a second end;

a second part (4) of the transparietal tube having a first end and a second end, wherein the first part (2) of the transparietal tube and the second part (4) of the transparietal tube are fitted to each other for allowing to induce a relative shifting in an axial direction of the first part (2) of the transparietal tube relative to the second part (4) of the transparietal tube such that the shifting is not spontaneously reversible;

a skin collar (6) attached to and holding the first end of the first part (2) of the transparietal tube against an outside surface of a skin;

a intravisceral collar (8) attached to and holding the first end of the second part (4) of the transparietal tube against the internal wall of a hollow organ, wherein the intravisceral collar (8) is constructed such that a shape of the intravisceral collar (8) is elastically deformable to allow the intravisceral collar (8) to pass inside the hollow organ directly from an outside of a patient's body;

a screw connection and tapping (26) furnished on the first part (2) of the transparietal tube and on the second part (4) of the transparietal tube, wherein the screw connection (26) is engageable from the outside towards the inside of the transparietal tube to enable a making of changes of a relative position of the first part (2) of the transparietal tube relative to the second part (4) of the transparietal tube such as to enable an increase or a decrease a length of the transparietal tube according to a cumulated thickness of a fascia (1) of a patient crossed, both at a time of installation of the transparietal tube and after the transparietal tube has been installed on the patient, and wherein a change in the length of the transparietal tube is taken up inside the thickness of the fascia (1) of the patient crossed by the transparietal tube, wherein a relative mobility between the first part (2) of the transparietal tube and the second part (4) of the transparietal tube is obtained by screwing the screw connection and tapping (26), wherein the second part (4) of the transparietal tube is furnished with a non circular axial opening (18) that constitutes a nesting organ, in order for the transparietal tube to be rendered immobile in a rotational direction by the practitioner using a pusher (16), which pusher (16) can be introduced inside the said non circular axial opening (18) and which pusher comprises at least one area of complementary cross-section.

22. The device according to claim 21 further comprising a spontaneously closing valve (22) disposed on the first end of the second part (4) of the transparietal tube;

a movable shutter disposed on the first end of the first part (4) of the transparietal tube.

23. A kit for inosculation of a hollow organ to the skin, comprising a first part (2) of a transparietal tube having a first end and a second end;

a second part (4) of the transparietal tube having a first end and a second end, wherein the first part (2) of the transparietal tube and the second part (4) of the transparietal tube are fitted to each other for allowing to induce a relative shifting in an axial direction of the first part (2) of the transparietal tube relative to the second part (4) of the transparietal tube such that the shifting is not spontaneously reversible;

a skin collar (6) attached to and holding the first end of the first part (2) of the transparietal tube against an outside surface of a skin;

an intravisceral collar (8) attached to and holding the first end of the second part (4) of the transparietal tube against the internal wall of a hollow organ, wherein the intravisceral collar (8) is constructed such that a shape of the intravisceral collar (8) is elastically deformable to allow the intravisceral collar (8) to pass inside the hollow organ directly from an outside of a patient's body;

an axial opening (18) having a non circular section and disposed in the second part (4) of the transparietal tube;

a pusher (16) having a first end and having a second end and including a non circular section between the first end and the second end of the pusher (16), wherein the non-circular section is constructed to traverse the axial opening (18) of complementary shape in the second part (4) of the transparietal tube, in order to render the second part (4) of the transparietal tube immobile in a rotational direction, wherein a shape of the intravisceral collar (8) is changeable by means of the pusher (16), wherein the pusher is introduceable inside the transparietal tube, wherein the second part (4) of the transparietal tube is constructed to enable the transparietal tube to be gripped by the pusher (16) in order to render the transparietal tube immobile for allowing to adapt the length of transparietal tube using the pusher (16) at least initially when the transparietal tube is installed on the patient;

a screw connection and tapping (26) furnished on the first part (2) of the transparietal tube and on the second part (4) of the transparietal tube, wherein the screw connection (26) is engageable from the outside towards the inside of the transparietal tube to enable a making of changes of a relative position of the first part (2) of the transparietal tube relative to the second part (4) of the transparietal tube such as to enable an increase or a decrease a length of the transparietal tube according to a cumulated thickness of a fascia (1) of a patient crossed, both at a time of installation of the transparietal tube and after the transparietal tube has been installed on the patient, and wherein a change in the length of the transparietal tube is taken up inside the thickness of the fascia (1) of the patient crossed by the transparietal tube.

24. A method for inosculating of a hollow organ to the skin, comprising the following steps:

furnishing a first part (2) of a transparietal tube having a first end and a second end;

furnishing a second part (4) of the transparietal tube having a first end and a second end;

fitting the first part (2) of the transparietal tube and the second part (4) of the transparietal tube to each other for allowing to induce a relative shifting in an axial direction of the first part (2) of the transparietal tube relative to the second part (4) of the transparietal tube such that the shifting is not spontaneously reversible;

attaching a skin collar (6) to and holding the first end of the first part (2) of the transparietal tube against an outside surface of a skin;

attaching an intravisceral collar (8) to and holding the first end of the second part (4) of the transparietal tube against the internal wall of a hollow organ, wherein the intravisceral collar (8) is constructed such that a shape of the intravisceral collar (8) is elastically deformable to allow the intravisceral collar (8) to pass inside the hollow organ directly from an outside of a patient's body installing the transparietal tube on the patient;

installing the transparietal tube on the patient;

furnishing an axial opening (18) having a non circular section in the second part (4) of the transparietal tube;

furnishing a pusher (16) having a first end and having a second end;

including a non circular section between the first end and the second end of the pusher (16);

constructing the non-circular section to be able to traverse the axial opening (18) of complementary shape in the second part (4) of the transparietal tube, in order to render the second part (4) of the transparietal tube immobile in a rotational direction;

introducing the pusher (16) inside the transparietal tube;

changing a shape of the intravisceral collar (8) by means of the pusher (16);

constructing the second part (4) of the transparietal tube to enable the transparietal tube to be gripped by the pusher (16);

gripping the transparietal tube with the pusher;

rendering the transparietal tube immobile for allowing to adapt the length of the transparietal tube using the pusher (16);

furnishing a screw connection and tapping (26) on the first part (2) of the transparietal tube and on the second part (4) of the transparietal tube;

engaging the screw connection (26) from the outside towards the inside of the transparietal tube;

screwing the first part (2) of the transparietal tube relative to the second part (4) of the transparietal tube;

making changes of a relative position of the first part (2) of the transparietal tube relative to the second part (4) of the transparietal tube such as to enable an increase or a decrease a length of the transparietal tube according to a cumulated thickness of a fascia (1) of a patient crossed, both at a time of installation of the transparietal tube and after the transparietal tube has been installed on the patient;

taking up a change in the length of the transparietal tube inside the thickness of the fascia (1) of the patient crossed by the transparietal tube.

25. The method for inosculating of a hollow organ to the skin, according to claim 24 further comprising the following steps:

furnishing the first part (2) of the transparietal tube telescopic relative to the second part (4) of the transparietal tube;

obtaining immobilization of the second part (4) of the transparietal tube by means of the pusher (16);

pushing the intravisceral collar (8) out of shape when installing the transparietal tube on the patient.

26. The method for inosculating of a hollow organ to the skin, according to claim 24 further comprising the following steps:

furnishing a spontaneous closing valve (22) disposed on a first end of the second part (4) of the transparietal tube;

moving a movable shutter (24) disposed at the first end of the first part of the transparietal tube;

forming the intravisceral collar (8) as a hollow body;

furnishing lateral openings (28) to the hollow body;

gripping the skin collar (6) from the outside;

immobilizing the first part (2) of the transparietal tube.

* * * * *